United States Patent
Nadam

[11] Patent Number: 5,807,301
[45] Date of Patent: Sep. 15, 1998

[54] DISPOSABLE DEVICE FOR SAFE CLEANING OF THE EAR

[76] Inventor: Igal Nadam, 37 Abulafia Street, Tel Aviv, Israel

[21] Appl. No.: 852,819

[22] Filed: May 7, 1997

[30] Foreign Application Priority Data

May 9, 1996 [IL] Israel ............................... 118207

[51] Int. Cl.⁶ .................................................. A61M 35/00
[52] U.S. Cl. .................................. 604/1; 223/101; 401/7; 15/227
[58] Field of Search ............................ D3/29; 604/1–3; 600/38; 223/101; 401/7; 15/227

[56] References Cited

U.S. PATENT DOCUMENTS

| 1,297,784 | 3/1919 | Birnbaum | 401/7 |
| 4,665,901 | 5/1987 | Spector | 128/62 |
| 5,045,073 | 9/1991 | Wagner | 604/310 |
| 5,604,952 | 2/1997 | Zeleznick | 15/167.1 |

*Primary Examiner*—John G. Weiss
*Assistant Examiner*—Dennis Ruhl
*Attorney, Agent, or Firm*—Lowe Hauptman Gopstein Gilman & Berner

[57] ABSTRACT

A disposable ear cleaning device includes a thimble having a rigid extension protruding from a top portion thereof with a layer of cotton or other soft material wrapped around the protrusion.

13 Claims, 1 Drawing Sheet

DISPOSABLE DEVICE FOR SAFE CLEANING OF THE EAR

FIELD OF THE INVENTION

The present invention relates to a device for safe cleaning of the ear. More specifically the invention relates to a disposable ear cleaning device comprised of an elastic thimble containing, preferably as an integral part of the thimble, an extension of a rigid or semi-rigid material preferably with a rounded end. An appropriate layer of cotton for cleaning the ear is wrapped on the extension. The length of this extension does not exceed that of the distance between the ear cap and the ear drum. This extension is meant to be inserted into the ear and thus provides a device for safely cleaning the ear.

BACKGROUND OF THE INVENTION

The present well known ear cleaning devices are plastic or wooden sticks having tightly wrapped cotton on their tips. The cotton tips are inserted into the ear for the purpose of cleaning any dirt that has accumulated in the ear cap.

Many cases of ear injuries, as a result of using ear cleaning devices, have been reported. Some injuries are due to the fact that the stick, whose tip is not rounded, sometimes pokes through the cotton and scratches the inner surface of the ear. The more serious injuries are those caused to the ear drum by inserting the cleaning stick too deep into the ear. A person inserting the ear cleaner into an ear that is not his own, as in the case of cleaning a babys' ear, has no feeling as to how deep to insert the cleaner and there is danger of inserting the ear cleaner too deep.

As a means of safety, some of the known devices are made with clover shaped cotton tips whereas the wider part of the cotton tip is meant to prevent excessive insertion of the stick into the ear avoid harming the ear drum. The clover shaped cotton tip is not effective in cases where too much force is applied in inserting the stick in the ear, because the cotton is soft and yields to the applied force, enabling excessive insertion of the stick. Surprisingly, the present invention overcomes the above mentioned disadvantages and provides a completely safe device for cleaning the ear.

The present invention relates to a device for safe cleaning of the ear, which is comprised of a thimble with an extension protruding from its top, the thimble and extension preferably comprising an integral unit, wherein the extension, preferably with a rounded tip, is wrapped with cotton used to clean the ear. The thimble described in the present invention is fitted on the finger and the cotton wrapped extension protruding from its top is intended for insertion into the ear with the help of that finger. The length of the extension does not exceed that of the distance between the ear cap and the ear drum, making it impossible to insert the cottoned tip too deep into the ear because the width of the finger directly behind the extension will not permit it.

The distance between the ear cap and the ear drum in a mans' ear varies with age. The above mentioned extension can be made in different lengths, thus allowing for adaption of the device to different sized ears (babys' ears as opposed to adults, etc.). The rounded tip of the extension and the fact that the extension is an integral part of the thimble, making it impossible for it to break off in the ear, are properties of the present invention that render it a completely safe ear cleaning device.

SUMMARY OF THE INVENTION

The present invention relates to a disposable safe ear cleaning device comprised of a thimble preferably made of flexible material having a rigid or semi-rigid extension protruding from its top, preferably with a rounded tip, wrapped with cotton. The thimble and the extension preferably comprise one integral unit wherein the thimble is made of a flexible material such as rubber or flexible plastic and may contain several incisions for easier stretching and fitting on the finger, and the extension is made of a non flexible material. The extension has a rounded tip and is tightly wrapped with cotton or any other material used to clean the ear wherein the cotton may be wound to produce any shaped tip, such as a clover shaped or a rounded tip.

Safe cleaning of the ear with the device described in the present invention is ensured by the use of the round tipped extension that is to be inserted into the ear which will not scratch the ear even if it pokes through the cotton and which will not break off in the ear because it is an integral unit of the thimble. Furthermore, safety is ensured by the fact that the length of the extension does not exceed that of the length between the ear cap and the ear drum, making it impossible to insert the cottoned tip too deep into the ear.

DETAILED DESCRIPTION OF THE INVENTION

The present invention describes a disposable device for safe cleaning of the ear. The device in the present invention is preferably one integral unit comprising a thimble made of flexible material, such as rubber or flexible plastic, which may be slitted on the bottom for easy fitting on the finger,and an extension, preferably round tipped, made of non flexible material. Wrapped on the extension tip may be cotton, or any other material suitable for cleaning the ear, wound to form any desirable shape such as a clover shape etc.

The ear cleaning device described in the present invention is used by fitting the thimble on the finger and with the help of that finger inserting the cotton wrapped extension in the ear.

As opposed to other devices for cleaning the ear that are marketed today, the device described in the present invention offers safe cleaning of the ear. The safety of the device lies mainly in three of its features:

1. The length of the extension meant to be inserted into the ear does not exceed that of the distance between the ear cap and the ear drum. Directly behind this extension is the finger fitted with the extension bearing thimble. Since the finger is wider than the ear cap, the extension cannot be inserted into the ear further than its length, making it impossible for the extension tip to reach the ear drum.

2. The hardened cotton wrapped extension is rounded at its tip so that should the tip poke through the cotton wrapping, the hardened tip will not scratch the ear surface.

3. In its preferred embodiment the ear cleaning device of this invention comprises a thimble and an extension which are one integral unit. As such, there is no danger of the extension breaking off while being inserted in the ear.

The invention will be further described in detail by the following drawings. These drawings do not intend to limit the scope of the invention but to demonstrate and clarify it only.

DETAILED DESCRIPTION OF THE DRAWINGS

Figure 1:
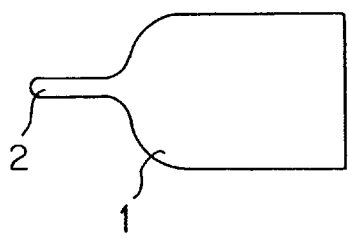
FIG. 1 is a side view of the thimble and its extension of the ear cleaning device of this invention.

FIG. 1 is a side view of the thimble (1) and the extension (2) protruding from its top.

Figure 1A:
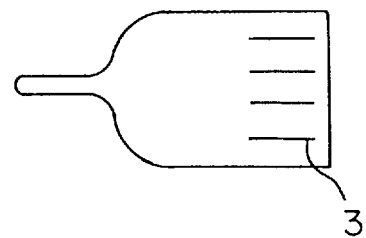
FIG. 1a is a side view of a preferred embodiment of the ear cleaning device of this invention.

FIG. 1a is a side view of a preferred embodiment of the invention wherein the thimble of the ear cleaning device contains incisions (3) for easier fitting on the finger.

Figure 2:
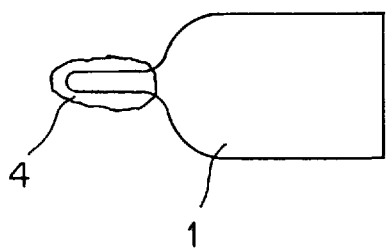
FIG. 2 is a side view of the ear cleaning device of this invention.

FIG. 2 is a side view of the ear cleaning device of this invention wherein the extension of the thimble (1) is wrapped with cotton (4) or any other material suitable for cleaning the ear.

Figure 3:
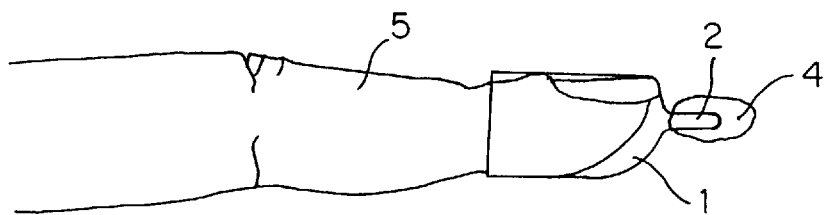
FIG. 3 is a side view of the ear cleaning device of this invention fitted on a finger.

FIG. 3 is a side view of the the thimble (1) of the ear cleaning device of this invention, fitted on a finger (5) for inserting the cotton (4) wrapped extension (2) in to the ear.

I claim:

1. A disposable device for safe cleaning of an ear, comprising a thimble having a rigid or semi-rigid extension protruding from a forward end thereof, said extension including a tip wrapped with a layer of soft material for cleaning the ear.

2. A disposable device for safe cleaning of the ear according to claim 1 wherein the thimble is made of a flexible material including one of rubber and a flexible plastic.

3. A disposable device for safe cleaning of the ear according to claim 1 wherein the thimble includes incisions to facilitate stretching and fitting of the thimble on the finger.

4. A disposable device for safe cleaning of the ear according to claim 1 wherein the extension has a rounded tip.

5. A disposable device for save cleaning of the ear according to claim 1 wherein the thimble and the extension with tip comprise one integral unit.

6. The disposable device of claim 1, wherein said soft material is cotton.

7. The disposable device of claim 1, wherein said soft material is formed with randomly oriented fibers.

8. The disposable device of claim 3, wherein said incisions are longitudinal incisions formed adjacent an open end of the thimble.

9. The disposable device of claim 1, wherein the length of said tip is less than one-half the overall length of the thimble extending rearwardly from the forward end.

10. The disposable device of claim 1, wherein the forward end of the thimble from which the tip projects is completely enclosed.

11. The disposable device of claim 3, wherein incisions are formed only in a rear portion of the thimble located opposite the said forward end.

12. The disposable device of claim 1, wherein said tip is entirely embedded in said soft material without any portion protruding forwardly thereof.

13. A method of safely cleaning an ear, comprising the steps of:
(a) inserting a finger into a thimble having a rigid or semi-rigid extension protruding from a forward end thereof, said extension including a tip wrapped with a layer of soft material for cleaning the ear;
(b) guiding the finger towards the ear so that the tip enters into the ear; and
(c) cleaning said ear by appropriately manipulating said finger to move the tip within the ear.

* * * * *